United States Patent [19]

Kominami et al.

[11] 3,950,434

[45] Apr. 13, 1976

[54] METHOD FOR PRODUCING BIPHENYLS

[75] Inventors: Naoya Kominami, Tokyo; Nobuhiro Tamura, Oi; Etsuo Yamamoto, Tokyo, all of Japan

[73] Assignee: Asahi Kasei Kogyo Kabushiki Kaisha, Osaka, Japan

[22] Filed: June 28, 1973

[21] Appl. No.: 374,769

Related U.S. Application Data

[63] Continuation of Ser. No. 62,656, Aug. 10, 1970, abandoned.

[30] Foreign Application Priority Data

Aug. 11, 1969 Japan.............................. 44-62939
Sept. 29, 1969 Japan.............................. 44-76911

[52] U.S. Cl.... 260/613 R; 260/346.8 R; 260/524 R; 260/580; 260/645; 260/649 DP; 260/670
[51] Int. Cl.² .................. C07C 15/14; C07C 25/00; C07C 43/20; C07C 79/10
[58] Field of Search.......... 260/613 R, 649 DP, 670, 260/645

[56] References Cited

UNITED STATES PATENTS

| | | | |
|---|---|---|---|
| 3,145,237 | 8/1964 | Helden et al. ....................... | 260/670 |
| 3,401,207 | 9/1968 | Selwitz................................ | 260/670 |
| 3,578,716 | 5/1971 | Robinson............................. | 260/670 |
| 3,591,645 | 7/1971 | Selwitz............................ | 260/649 D |
| 3,636,170 | 1/1972 | Notaro et al..................... | 260/649 D |
| 3,728,409 | 4/1973 | Selwitz................................ | 260/670 |

OTHER PUBLICATIONS

Davidson et. al., J. Chem. Soc. (A), 1968, pp. 1324–1330.
Davidson, et al., (I), Chem. Ind., 1967, p. 1361–1966, p. 457.

*Primary Examiner*—James O. Thomas, Jr.
*Assistant Examiner*—Nicky Chan
*Attorney, Agent, or Firm*—Armstrong, Nikaido & Wegner

[57] ABSTRACT

Biphenyl or nucleus-substituted biphenyl can be prepared from benzene or nucleus-substituted benzene and oxygen or oxygen-containing gas in one step according to an equation

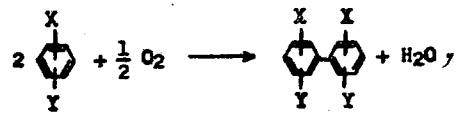

wherein X is H, lower alkyl having 1 to 6 carbon atoms Cl, $NO_2$, or lower alkoxy having 1 – 3 carbon atoms and Y is H or $CH_3$, with excellent yield by heating the reactants in the presence, as a catalyst, of palladium or a palladium compound and sulfuric acid or sulfuric acid and a lower saturated fatty acid added to the reaction system and further in the presence or in the absence of an alkali metal salt.

6 Claims, No Drawings

METHOD FOR PRODUCING BIPHENYLS

CROSS REFERENCE TO RELATED APPLICATIONS

This application is a Continuation of our copending Application Ser. No. 62,656, filed Aug. 10, 1970 and now abandoned.

This invention relates to a method for producing biphenyls which are useful as raw materials for novel compounds or novel high molecular compounds, with excellent efficiency in accordance with a following reaction equation

wherein X is a member selected from the group consisting of H, lower alkyl having 1 – 6 carbon atoms, Cl, $NO_2$ and lower alkoxy having 1 – 3 carbon atoms and Y is a member selected from the group consisting of H and $CH_3$.

Heretofore, there has never been any commercially advantageous method for producing biphenyls known. If anything, a synthetizing method of biphenyl from chlorobenzene and metallic copper, and a method which relies on high temperature reaction of benzene, etc. were known. These methods cannot be applied to nucleus-substituted benzene even though they can be applied in case of benzene. Thus they cannot be said to be commercially useful processes in the aspects of raw material and operation.

On the other hand, methods which use palladium compounds have been recently disclosed, for example a method for producing a bitolyl which uses palladium acetate and mercuric acetate [J.O.C. 34 18 (1969)], a method for producing biphenyls from benzenes which uses palladium chloride and sodium acetate (U.S. Pat. No. 3,145,237), etc.

However, in these methods, yields of biphenyl per used palladium are less than 100 % or at the highest 100 % and the fact that palladium does not act as a catalyst is apparent. If palladium acts only as a reactant, it is necessary to return palladium to the reaction after the steps of recovery and regeneration.

From the viewpoint of cost, the circulation of extremely precious metal is commercially disadvantageous if the loss during the process is considered.

In this connection, the inventors of the present invention have been investigating a method in which palladium is recycled within a reaction system in order to overcome the above-mentioned methods, and have completed the method of the present invention.

It is, therefore, an object of the present invention to provide a method for producing biphenyl or bi(substituted phenyl) with a yield higher than any conventional methods.

According to the method of present invention, biphenyl or nucleus-substituted biphenyl can be produced with a high yield by reacting benzene or nucleus-substituted benzene with oxygen in the presence of a catalyst comprising palladium or a palladium compound and a small amount of sulfuric acid added to the reaction system. More specifically, a method for producing biphenyls with a high yield and a high selectivity is provided by the present invention, which method is characterized in using, as a catalyst, palladium or a palladium compound alone or a combination of a palladium compound and an alkali metal salt and adding sulfuric acid or sulfuric acid and a lower saturated alkanoic acid such as acetic acid or the like to the reaction system in producing biphenyl or nucleus-substituted biphenyl from benzene or nucleus-substituted benzene and oxygen or an oxygen-containing gas.

In the practice of the present invention, the palladium compounds, as a principal catalyst, include inorganic acid salts such as sulfate, nitrate, phosphate, etc. and organic acid salts such as acetate, propionate etc. The alkali salts, suitable as a co-catalyst, include inorganic salts of lithium, sodium, potassium, rubidium and cesium such as sulfate, nitrate, phosphate, etc. and organic salts of the foregoing metals such as acetate, propionate, etc.

The amount of these co-catalysts to be added in the practice is in the range of 1,000 to 1/100 expressed by atomic ratio of alkali is palladium. However, it is preferable that the amount is in the range of 100 to 1/50.

These principal catalysts and co-catalysts can be used in the reaction without supported on a carrier but it is preferable that they are supported on a carrier. The carriers used in this case may bee any porous carriers conventionally used, such as active carbon, silica, alumina, silica alumina, etc.

Further in the method of the present invention, metallic palladium can be used as a catalyst. It can be prepared easily by reducing a palladium compound (in this case any of chlorides etc. can be used) supported on a porous carrier, with a reducing agent such as hydrogen, formalin, hydrazine, etc.

The amount of sulfuric acid used in the practice of the present invention varies according to the raw material subjected to the reaction but it is preferably in the range of 0.4 to 0.001 mol and most preferably in the range of 0.2 to 0.005 mol per one mol of the raw material aromatic compound.

Materials which may be added to reaction system together with sulfuric acid in order to make the raw material aromatic compound uniform, include lower saturated alkanoic acids such as acetic acid, propionic acid etc. These additives are useful for properly adjusting the reaction but if their amount is too excessive, side reactions are promoted. Therefore, the amount to be used is preferably less than 2 moles per mol of aromatic compound.

Aromatic compounds, as the raw material in the practice of the present invention, include benzene, toluene, ethylbenzene, o-, m- or p-xylene, cumene, chlorobenzene, nitrobenzene, o-, m-, or p-nitrotoluene and anisole.

Oxygen can be used in pure or diluted state. As gases other than oxygen which may be existent together with oxygen are nitrogen, carbon dioxide, and other gases inert to the reaction. However, if the partial pressure of oxygen becomes too low, reaction velocity is reduced and side reaction tends to occur. So there is a limit of coexistence of these gases. So long as oxygen partial pressure is at least 5 $kg/cm^2$, any amount of diluent can be used.

The method of the present invention can be carried out at reaction temperature of 30°C – 300°C preferably 50°C – 200°C in the practice.

As for oxygen pressure, it must be higher than 5 kg/cm² and is preferably to be in the range of 10 – 60 kg/cm², because greater oxygen density is preferable.

As for reaction manner, a process in which liquid and gas flow, a process in which liquid and gas are mixed with stirring, etc. are preferable.

It is well known that biphenyl has utility in liquid heating media but nucleus-substituted biphenyls can be used as a raw material for producing polyesters, polyamides, polyimides, etc.

For example, products produced according to following formulae are useful for such purposes

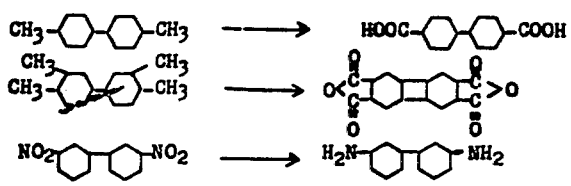

The present invention is further illustrated by the following non-limitative examples.

EXAMPLE 1

To a solution of 0.1 g of palladium chloride dissolved in a suitable amount of dilute hydrochloric acid, was added 10 c.c. of granular silica gel, and the mixture was evaporated to dryness. The resultant mixture was then reduced by adding thereto an alkaline solution of hydrazine hydrate, washed fully with water and dried. 10 c.c. of solids thus obtained was dipped in an aqueous solution containing 0.2 g of potassium acetate and evaporated to dryness to give a catalyst.

10 c.c. of the catalyst thus prepared was fed into a 50 c.c. microbomb, together with 10 g of benzene, 5 g of acetic acid and 0.2 g of concentrated sulfuric acid, and the bomb was sealed. Oxygen was introduced therein through an upper valve till its pressure reached 40 kg/cm². The bomb was then placed in an oil bath of shaking type whose temperature had been controlled to 100°C. After the reaction was carried out for 20 hours, the catalyst was separated and removed. The reaction mixture containing unreacted benzene and acetic acid was cooled and filtered. The resultant filtrate was evaporated to give 2.1 g of biphenyl

Control 1

The reaction was carried out using the same catalyst and the same conditions with those of Example 1, but no sulfuric acid was added. As a result, no biphenyl was formed, but a small amount of phenyl acetate was formed.

EXAMPLE 2

10 c.c. of granular silica gel was added to an aqueous acetic acid solution in which 0.1 g of palladium acetate and 0.2 g of potassium acetate were dissolved, and the mixture was evaporated to dryness on a water bath. 10 c.c. of a catalyst thus prepared, 10 c.c. of benzene, 5 c.c. of acetic acid and 0.2 c.c. of cf conc. sulfuric acid were fed into a 50 c.c. microbomb, and the bomb was sealed. Oxygen was introduced therein through an upper valve till its pressure reached 40 kg/cm². The bomb was then placed in an oil bath of shaking type whose temperature had been controlled to 100°C. After the reaction was carried out for 20 hours, the catalyst was separated, and biphenyl was then separated from the mixture of unreacted benzene and acetic acid by filtration and distillation. As a result, it was confirmed that 3.15 g of biphenyl was formed. No other product was observed.

Control 2

The reaction was carried out in a similar way to Example 2 except that no sulfuric acid was used. No formation of biphenyl was observed. A small amount of phenyl acetate was formed.

EXAMPLES 3 – 12 and 26

Experiments relative to various kinds of catalysts were carried out using the same apparatus and the same method with those of Example 1. Thus, results as shown in the Table were obtained. The reaction time was 20 hours in all cases, and preparation of catalyst was carried out in a similar manner to that of Example 1.

EXAMPLES 13 – 25

Experiments relative to various kinds of catalysts were carried out using the same apparatus and the same method with those of Example 2. The results are shown in the Table. The reaction time was 20 hours as in Example 2, and preparation of catalyst was all carried out by the same method with that of Example 2.

Table

| | | | Feeding conditions | | | | | | |
|---|---|---|---|---|---|---|---|---|---|
| Example | Amount of catalyst used (g) | amount of carrier used (c.c.) | Aromatic raw material (g) | Conc. H₂SO₄ (g) | Other organic acid (g) | Oxygen (kg/cm²) | Reaction temperature (°C) | Result of reaction | |
| | | | | | | | | Product | Yield |
| 3 | Pd - LiOAc (0.1) (0.5) | Silica (10) | Benzene 10 | 0.2 | Acetic acid 10 | 40 | 120 | Biphenyl | 2.7 |
| 4 | Pd - KNO₃ (0.2) (0.5) | Silica (20) | Nitrobenzene 10 | 1.2 | " 10 | " | 150 | 3,3'-Dinitrobiphenyl | 1.9 |
| 5 | Pd (0.1) | Alumina (5) | m-Xylene 10 | 0.2 | " 5 | " | 100 | 2,4,2',4'-Tetramethylbiphenyl | 0.6 |
| 6 | Pd - NaH₂PO₄ (0.1) (0.3) | Activated carbon (10) | p-Xylene 10 | 0.1 | " 5 | " | 80 | 2,5,2',5'-Tetramethylbiphenyl | 0.7 |
| 7 | Pd - CsOAc (0.2) (1.0) | Activated carbon (10) | Toluene 10 | 0.3 | " 2 | " | 70 | 2,2'-Dimethylbiphenyl 4,4'-Dimethylbiphenyl | 0.3 0.4 |
| 8 | Pd - RbSO₄ (0.05) (0.1) | Silica (5) | o-Xylene 10 | 0.1 | " 2 | 20 | 70 | 3,4,3',4'-Tetramethylbiphenyl | 0.5 |

Table-continued

| Example | Amount of catalyst used (g) | amount of carrier used (c.c.) | Aromatic raw material (g) | Conc. H₂SO₄ (g) | Other organic acid (g) | Oxygen (kg/cm²) | Reaction temperature (°C) | Product | Yield |
|---|---|---|---|---|---|---|---|---|---|
| 9 | Pd - LiNO₃ (0.1) (0.5) | Silica-alumina (10) | Benzene 10 | 0.5 | Propionic acid 5 | " | 130 | Biphenyl | 1.4 |
| 10 | Pd - NaOAc - KOAc (0.1) (0.2) (0.2) | Activated carbon (10) | Anisole 10 | 0.5 | Acetic acid 10 | " | 120 | 4,4'-Dimethoxy-biphenyl | 0.6 |
| 11 | Pd - KH₂PO₄ (0.1) (0.1) | Silica (10) | Chlorobenzene 10 | 0.5 | " 10 | " | 100 | 4,4'-Dichloro-biphenyl | 0.7 |
| 12 | Pd - CsSO₄ (0.05) (0.3) | Silica (5) | o-Nitrotoluene 10 | 1.5 | Acetic acid 10 | 40 | 150 | 2,2'-Dimethyl-3,3'-dinitro-biphenyl | 0.5 |
| | | | | | | | | 4,4'-Dimethyl-3,3'-dinitrobiphenyl | 0.3 |
| 13 | PdSO₄ (0.1) | Activated carbon (10) | m-Xylene 10 | 0.2 | " 5 | " | 100 | 2,4,2',4'-Tetramethylbiphenyl | 1.3 |
| 14 | PdOAc - NaH₂PO₄ (0.1) (0.2) | " (10) | Toluene 15 | 0.3 | " 5 | " | 80 | 2,2'-Dimethyl-biphenyl | 0.6 |
| | | | | | | | | 4,4'-Dimethyl-biphenyl | 0.8 |
| 15 | PdOCOC₂H₅ - CsOAc (0.1) (0.2) | Silica (10) | Anisole 10 | 0.5 | " 10 | " | 120 | 4,4'-Dimethoxy-biphenyl | 1.5 |
| 16 | PdNO₃ - RbSO₄ (0.05) (0.1) | Alumina (5) | p-Xylene 10 | 0.2 | " 5 | 20 | 80 | 2,5,2',5'-Tetramethylbiphenyl | 0.9 |
| 17 | PdOAc - LiNO₃ (0.1) (0.3) | Silica (10) | o-Xylene 5 | 0.1 | " 2 | 40 | 60 | 3,4,3',4'-Tetramethylbiphenyl | 0.7 |
| 18 | PdOAc - NaOAc - CsOAc (0.05) (0.2) (0.2) | " (5) | Benzene 5 | 0.5 | " 5 | " | 130 | Biphenyl | 2.5 |
| 19 | PdPO₄ - KH₂PO₄ (0.1) (0.3) | " (10) | Chlorobenzene 10 | 1.0 | " 5 | " | 150 | 4,4'-Dichloro-biphenyl | 1.3 |
| 20 | PdNO₃ - CsSO₄ (0.05) (0.1) | activated carbon (5) | m-Nitrotoluene 10 | 1.0 | Acetic acid 5 | 40 | 130 | 3,3'-dinitro-5,5'-Dimethylbiphenyl | 2.2 |
| 21 | PdPO₄ (0.1) | " (10) | Benzene 10 | 0.2 | " 10 | " | 120 | Biphenyl | 0.7 |
| 22 | PdOAc - K₂SO₄ (0.1) (0.5) | Silica (10) | Toluene 10 | 0.2 | " 10 | " | 100 | 2,2'-Dimethyl-biphenyl | 0.9 |
| | | | | | | | | 4,4'-Dimethyl-biphenyl | 1.1 |
| 23 | PdOAc - CsOAc (0.05) (0.2) | " (10) | p-Nitrotoluene 5 | 0.5 | " 5 | " | 150 | 2,2'-dimethyl-5,5'-Dinitrobiphenyl | 1.6 |
| 24 | PdPO₄ - NaH₂PO₄ (0.1) (0.3) | " (10) | o-Nitrotoluene 5 | 0.5 | " 5 | " | 150 | 2,2'-dimethyl-3,3'-Dinitrobiphenyl | 0.6 |
| | | | | | | | | 4,4'-dimethyl-3,3'-Dinitrobiphenyl | 0.8 |
| 25 | PdOAc - RbOAc (0.1) (0.5) | " (10) | o-Xylene 10 | 0.1 | " 10 | " | 100 | 3,4,3',4'-Tetramethylbiphenyl | 2.1 |
| 26 | Pd - RbOAc (0.05) (0.3) | Alumina (5) | Cumene 10 | 1.5 | — | " | 150 | 4,4'-Diisopropyl-biphenyl | 1.3 |

What is claimed is:

1. In a method for producing biphenyl compounds of the formula:

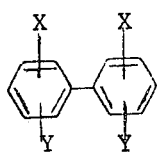

wherein X is H, lower alkyl having 1 to 6 carbon atoms, Cl, NO₂ or lower alkoxy having 1 to 3 carbon atoms and Y is H or CH₃ by heating to an elevated temperature a mono-nuclear aromatic compound of the formula:

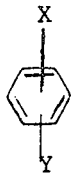

wherein X and Y are as defined aforesaid, in the presence of an oxygen containing gas and a catalytic amount of palladium or a palladium compound selected from the group consisting of palladium sulfate, nitrate, phosphate, acetate and propionate, the improvement comprising conducting the reaction in the presence of 0.001 – 0.4 mols, per mole of mono-nuclear aromatic compound, of sulfuric acid at a temperature in the range of 30°C – 300°C under an oxygen pressure of at least 5 kg/cm².

2. A method according to claim 1 in which a lower alkanoic acid is present along with the sulfuric acid.

3. A method according to claim 1 wherein a co-catalytic amount of an alkali metal salt is present along with the palladium of palladium compound.

4. A method according to claim 3 wherein said alkali metal salt is a member selected from the group consisting of sulfate, nitrate, phosphate, acetate and propionate, respectively of lithium, sodium, potassium, rubidium and cesium.

5. A method according to claim 1 wherein said palladium compound is palladium acetate.

6. A method according to claim 1 wherein the oxygen gas pressure is in the range of 10 – 60 kg/cm$^2$.

* * * * *